United States Patent
Kohler (12)

(10) Patent No.: US 6,238,667 B1
(45) Date of Patent: *May 29, 2001

(54) METHOD OF AFFINITY CROSS-LINKING BIOLOGICALLY ACTIVE IMMUNOGENIC PEPTIDES TO ANTIBODIES

(76) Inventor: Heinz Kohler, 5235 Athens Boonesboro Rd., Lexington, KY (US) 40509

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/070,907

(22) Filed: May 4, 1998

Related U.S. Application Data

(60) Provisional application No. 60/059,515, filed on Sep. 19, 1997.

(51) Int. Cl.[7] .......................... A61K 39/395; C07K 16/46
(52) U.S. Cl. ..................................... 424/179.1; 424/178.1; 530/402; 530/391.19; 530/391.5; 530/391.3; 530/391.1
(58) Field of Search ................................ 424/179.1, 402; 530/391.9, 391.5, 391.3, 391.1

(56) References Cited

U.S. PATENT DOCUMENTS 5,276,170 * 1/1994 Kirk et al. .............................. 552/8
5,596,081 * 1/1997 Haley et al. ........................ 530/391.1
5,800,991 * 9/1998 Haley et al. .............................. 435/6

OTHER PUBLICATIONS

Pandey et al, Journal of Immunological Methods, vol. 94 (1986), pp. 237–246.*

Luo et al, Nature Biotechnology, 16, (May 1998), 458–462.*

Pavlinkova. et al, Jrnl. of Immunological Methods, 201, (1997), 77–88.*

* cited by examiner

*Primary Examiner*—T. Wessendorf
(74) *Attorney, Agent, or Firm*—Antonelli, Terry, Stout & Kraus, LLP

(57) ABSTRACT

A method of affinity cross-linking a peptide to an antibody by photo-chemically activating an azido compound in a peptide including said azido compound; adding an antibody to the photochemically activated peptide; and allowing the photochemically activated peptide and the antibody to react. The azido compound has an affinity for a hydrophobic structure in the variable domain of the antibody which binds to nucleotides or nucleosides, binding the peptide into a native binding pocket of the immunoglobulin (Ig) structure of an antibody. The site of cross-linking is located away from the antigen binding site in the Fv domain avoiding the compromise of antigen recognition. A composition of a peptide cross-linked to an antibody is also disclosed.

17 Claims, 5 Drawing Sheets

T-cell RESPONSE TO PEPTIDE AND PEPTIDE (Fab) COMPLEX WITH AND WITHOUT NORMAL Ig

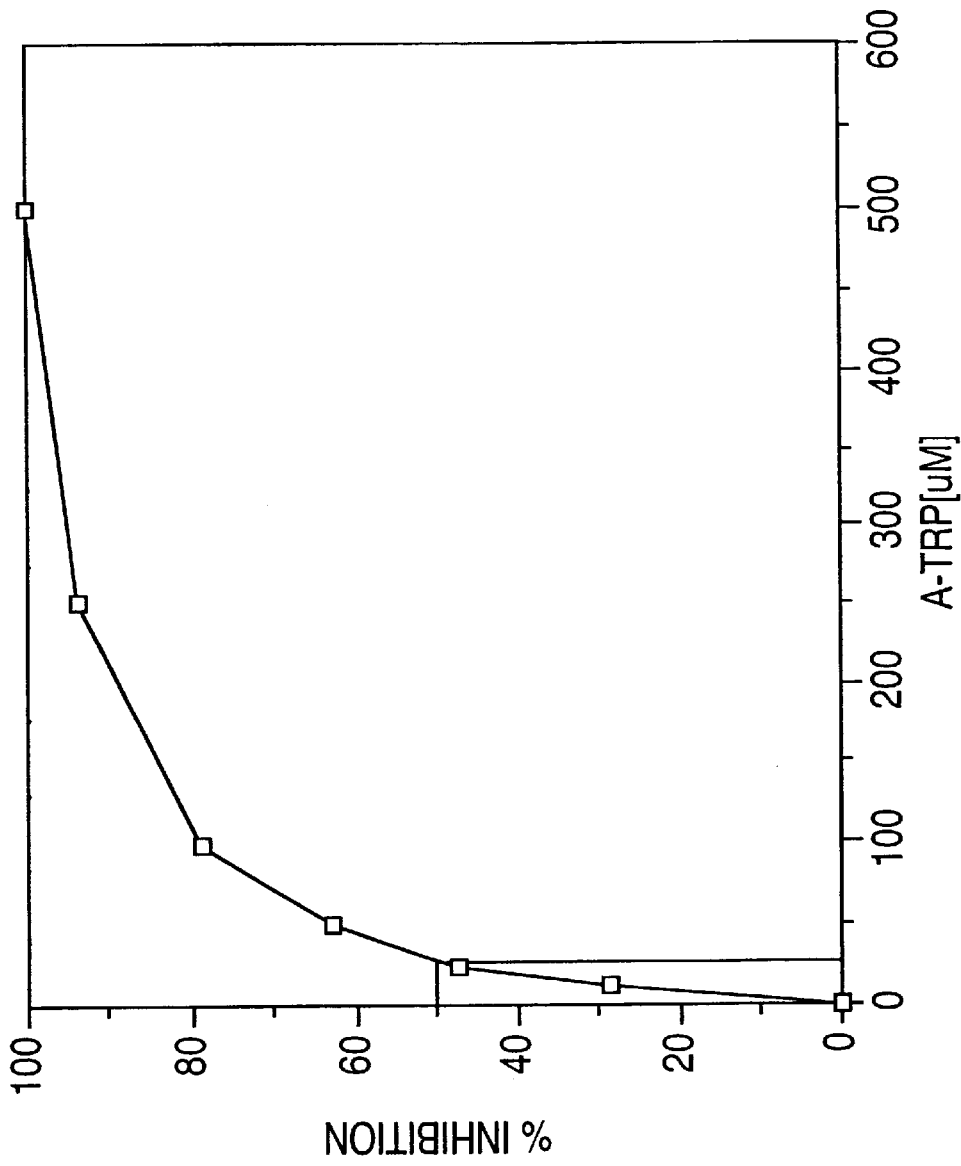
FIG. 5 INHIBITION OF AFFINITY-PHOTOBIOTINYLATION OF OKT3 BY 6-Azido TRP PHOTOLYSIS United States Patent 6,238,667 B1

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: AMINO ACID
      SEQUENCE DERIVED FROM Cd3 peptide

<400> SEQUENCE: 1

Lys Asn Arg Trp Glu Asp Pro Gly Lys Gln Leu Tyr Asn Val Glu Ala
 1               5                  10                  15

METHOD OF AFFINITY CROSS-LINKING BIOLOGICALLY ACTIVE IMMUNOGENIC PEPTIDES TO ANTIBODIES

This application is a continuation in part of provisional application U.S. Ser. No. 60/059,515 filed Sep. 19, 1997.

FIELD OF THE INVENTION

The present invention relates to a method of chemical cross-linking biologically active peptides to antibodies and a composition comprising one or more peptides cross-linked to an antibody. Specifically, the method attaches peptides to a unique affinity site of antibodies using photoreactive derivatives of peptides. These antibody-peptide complexes have immunostimulatory properties for B-cells and T-cells as a molecular adjuvant conjugated antibodies or antibody fragments. In addition the complexes may have biological properties to enhance antibody binding, facilitate membrane transport of antibodies or their fragments, and present B and T-cell epitopes to antigen presenting cells.

BACKGROUND OF THE INVENTION

Antibodies have been praised as "magic bullets" to combat disease. However, the promises made for antibodies were never fully realized. This-is in part due the fact that antibodies represent only one arm of the immune defense, where T-cells provide the other strategy in immune defense. However, antibodies are ideal targeting and delivery devices. They are adapted for long survival in blood, have sites which help vascular and tissue penetration and are functionally linked with a number of defense mechanisms of the innate immunity. One such mechanism is the complement system which helps to destroy pathogens and is involved in the regulation of immune responses. For example the complement fragment C3d binds to the CR2 receptor on B-cells, which is also the binding site for Epstein-Barr virus. Binding of Epstein-Barr virus to CR2 activates B-cells. Accumulated evidence has shown that the CR2 receptor (CD19/Cd20/CD81 complex) has an immunostimulatory role and is activated by C3d.

Another example of how antibodies can be used to enhance the immune response has been demonstrated by the work of Zanetti and Bona (Zanetti, M. Nature 355: 466–477, 1992; Zaghouani H.; Anderson S. A., Sperbeer K. E., Daian C. Kennedy R. C., Mayer L. and Bona C. A. 1995 Proc. Nat. Acad. Science U.S. 92: 631–635). These authors have replaced the CDR3 sequence of the Ig heavy chain with a sequence resembling T-cell and B-cell antigens (epitopes) using molecular biology methods and have shown that these modified antibodies induce potent immune response specific for the inserted groups. While this method of CDR replacement or antigenizing is effective, it requires manipulation of the genes encoding the immunoglobulin chains and expression of the modified antibodies with fermentation methods, both of which are expensive and time consuming.

The biological properties of the antibodies can be enhanced with respect to overall avidity for antigen and the ability to penetrate cellular and nuclear membranes. Antigen binding is enhanced by increasing the valency of antibodies such as in pentameric IgM antibodies. Valency and avidity is also increased in certain antibodies which are self binding or homophilic (Kang, C. Y., Cheng, H. L., Rudikoff, s. and Kohler, H. J. Exp. Med. 165:1332, 1987). Xiyun, A. N., Evans, S. V., Kaminki, M. J., fillies, S. F. D., Resifeld, R. A., Noughton, A. N. and Chapman, P. B. J. Immunol. 157: 1582–1588 (1996)). A peptide in the heavy chain variable region was identified which inhibited self-binding (Kang, C. Y. Brunck, T. K., Kiever-Emmons, T., Blalick, J. E. and Kohler, H., Science, 240: 1034–1036, 1988). The insertion of self-binding peptide sequence into an antibody endows the property of self-binding and increases the valency and overall avidity for the antigen.

Similarly the addition of a signal peptide to antibodies facilitates transmembrane transport as demonstrated by Rojas et al, Nature Biotechnology, 16: 370–375 (1998). Rojas et al. have generated a fusion protein which contained a 12 mer peptide and have shown that this protein has cell membrane permeability.

Antibodies have been used as delivery devices for several biologically active molecules, such as toxins, drugs and cytokines. Often fragments of antibodies, Fab or scFv, are preferred because of better tissue penetration and reduced "stickiness". Two methods to attach these molecules are known. One method is the design of a fusion gene and the expression of the fusion protein. This method requires extensive molecular biology engineering and depends typically on mammalian or bacterial expression systems in large scale fermentation. Another method of generating antibody complexes with other proteins or molecules relies on chemical cross-linking technologies. Usually hetero-bifunctional cross-linkers are used which cross-link the selected molecules at random sites on the immunoglobulin molecule. Hetero-bifunctional cross-linking is associated with two problems. First, the antibody structure is compromised by local protein denaturation at the sites of cross-linking. This leads to changes in half-life in blood and biodistribution and uptake by scavenger cells in lung and liver. The second problem is the potential loss of antigen binding by non-specific cross-linking to the antigen binding site.

A one chemical, site-specific cross-linking method exists (Rodwell, J D; Alvarez, V L; Lee, C; Lopes, A D; Goers, J W; King, H D; Powsner, H J; McKearn, T., *Proc. Natl. Acad. Sci.*, USA, 83:2632–6, 1986) which takes advantage of a unique carbohydrate site in the Fc domain of antibodies. This method has two disadvantages. First, cross-linking to the constant domain carbohydrate restricts this method to full-length antibodies and it cannot be used with variable domain fragments such as Fabs and scFvs. In addition, the method requires rather harsh chemical treatment using periodates for reducing the sugar to a reactive dialdehyde. This chemical reaction can damage other sensitive amino acid side chains, such as in tyrosine, in the Ig molecule leading to undesired changes in biodistribution or loss of antigen binding.

A variation of the carbohydrate site-specific cross-linking has been published by H. Hansen, et al., (Govindan, S V; Goldenberg, D M; Griffiths, G L; Leung, S O; Losman, M J; Hansen, H J., *Cancer Res.*, 55:5721–5725) who has introduced a carbohydrate signal sequence by site-directed mutagenesis in the variable domain of an Ig light chain. This sequence allows the attachment of sugars to a serine residue during synthesis of the mutated antibody. The reducing chemistry to generate dialdehydes is then used with the above described pitfalls. In addition the site-directed insertion of a carbohydrate signal sequence requires molecular biology engineering and expression systems. Furthermore, the site of insertion in the Fv domain has to be carefully selected in order to avoid compromising antigen binding and/or stability of the heavy-light chain dimer structure.

Rajagopolan, et at., (*PNAS*, 93:6019–24, 1996) described the affinity site on antibodies for ATP and Adenosine. U.S. Pat. No. 5,596,081 has issued for this site. A method of using azido-adenosine and Azido-ATP has been described by Pavlinkova, et al., (*J. Immun. Methods,* 201:77–88,1997). The active binding peptide of C3d (complement fragment) has been described by Lambris, et al., (*PNAS,* 82:4235–39, 1985). The synthesis of 5-azido-tryptophan has been described by Miles & Phillips (Miles, E. W. & Phillips, R. S., *Biochemistry,* 24:4694–703, 1985). A method of photo-labeling is reviewed by Potter and Haley (Potter, R. & Haley, B. E., *Meth. Enzymol,* 91:6130633, 1982).

The affinity-site cross-linking chemistry of the present invention overcomes prior art problems in the art and does not require the molecular engineering steps and fusion protein expression, since it allows to cross-link selected peptides to full-length antibodies or antibody fragments in one step using mild photo-reactive chemistry.

SUMMARY OF THE INVENTION

The present invention provides a method of affinity cross-linking a peptide to an antibody comprising the steps of (a) photo-chemically activating an azido compound in a peptide comprising said azido compound;

(b) adding an antibody to said photochemically activated peptide; and (c) allowing said photochemically activated peptide and said antibody to react, wherein said azido compound has an affinity for a hydrophobic structure in the variable domain of said antibody which binds to nucleotides or nucleosides, binding said peptide into a native binding pocket of the immunoglobulin (Ig) structure of an antibody, and wherein the site of cross-linking is located away from the antigen binding site in the Fv domain avoiding the compromise of antigen recognition.

In a preferred embodiment the photoreactive azido compound is created by oxidizing azido-adenosine with periodite to produce an azido-dialdehyde compound, wherein said dialdehyde is reacted via a Schiff-base reaction with primary amines of peptides of said antibody and photolyzed with UV light into an affinity site of said antibody.

In an alternative embodiment the azido compound is 5-azido tryptophan or 6-azido tryptophan, and wherein said azido compound is added to the C-terminal or N-terminal position of the peptide by standard peptide synthesis technology.

The invention also provides a composition and a pharmaceutical composition comprising a photochemically activated peptide having an N or C terminal azido compound, wherein said N or C terminal azido compound is crosslinked to an antibody and said azido compound has an affinity for a hydrophobic structure in the variable domain of said antibody which binds to nucleotides or nucleosides, binding said peptide into a native binding pocket of the immunoglobulin (Ig) structure of an antibody, and wherein the site of cross-linking is located away from the antigen binding site in the Fv domain avoiding the compromise of antigen recognition.

The invention of inserting biologically and immunologically active peptides into the variable domain of antibodies includes peptides which present T-cell and B-cell epitopes, comprise selfbinding, stimulate lymphocytes and allow transport across biological membranes.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE FIGURES

FIG. 5 shows Ig (OKT3 antibody) was first photolyzed with different concentrations of 6-azido-tryptophan followed by photolysis with 8-azido-adenosine-biotin. Reaction mixtures were dot-blotted on cellulose membrane and developed with avidin-horse-radish-peroxidase and substrate. Color density of dot-blots were measured and are plotted against concentration of 6-azido-tryptophan.

DETAILED DESCRIPTION OF THE INVENTION

Figure 1:
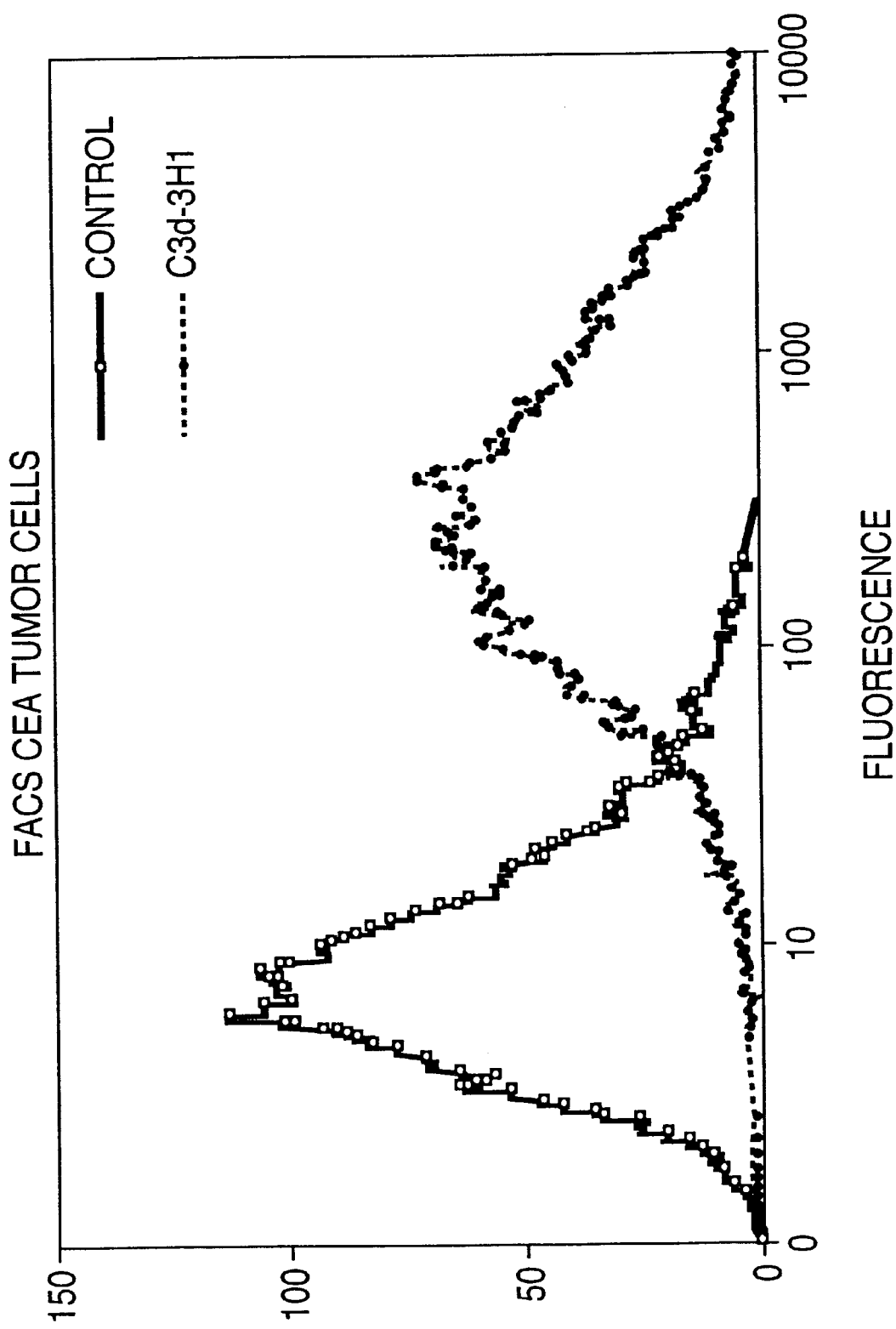
FIG. 1 shows that sera from mice immunized with C3d-3H1 were used in FACS of LS174T cells in a sandwich assay developed with FITC conjugated goat anti-mouse IgG. Control is a normal mouse serum. Cell number analyzed are plotted against relative fluorescence intensity on log10 scale.

The present invention describes a method for chemically cross-linking peptides to an affinity site on antibodies. The affinity site on antibodies is highly conserved, consisting of framework residues within the variable domains of heavy and light chains (Rajagopalan, et al., *PNAS,* 93:6019–24, 1996). The affinity site binds heterocyclic structures like purine and tryptophan compounds. Cross-linking is achieved via an azido group introduced into, for example, adenosine, tryptophan or ATP. The use of a photo-reactive azido compound for affinity cross-linking has been demonstrated for affinity cross-linking of biotin to an antibody (Pavlinkova, et al., *J. Immun. Methods,* 201:77–88, 1997).

The affinity-site cross-linking chemistry of the present invention overcomes prior art problems in the art and does not require the detailed molecular engineering and fusion protein expression steps, since it allows the cross-linking of any selected peptide to full-length antibodies or antibody fragments in one step using mild photo-reactive chemistry.

The site of cross-linking is located away from the antigen binding site in Fv domain avoiding compromising antigen recognition. Furthermore, cross-linking occurs into a native binding pocket while the overall Ig structure is kept intact. It is clear that this chemical method of cross-linking a peptide to an antibody is cost-saving and significantly less labor intensive than a molecular biology approach.

Thus, the present invention provides a method of affinity cross-linking a peptide to an antibody comprising the steps of
(a) photo-chemically activating an azido compound in a peptide comprising said azido compound;
(b) adding an antibody to said photochemically activated peptide; and
(c) allowing said photochemically activated peptide and said antibody to react, wherein said azido compound has an affinity for a hydrophobic structure in the variable domain of said antibody which binds to nucleotides or nucleosides, binding said peptide into a native binding pocket of the immunoglobulin (Ig) structure of an antibody, and wherein the site of cross-linking is located away from the antigen binding site in the Fv domain avoiding the compromise of antigen recognition. Each antibody has two variable domain structures and two molecules of peptides may be photo-inserted into one molecule of antibody.

The method of the invention may, further comprise a step of stabilizing the cross-linking with a mild reducing reagent. In a preferred embodiment the mild reducing agent is borohydrate.

The peptide of the invention may have a biological activity, such as immuno-stimulatory or immuno-regulatory activity. In a preferred embodiment the peptide is derived from the binding site region of cytokines or complement fragments. The peptide may comprise immunogenic epitopes for T-cells or B-cells. The peptide may, for example, be a hormone, ligand for cytokines or a binding site derived from natural ligands for cellular receptors. In a preferred embodiment the peptide is derived from C3d region 1217–1232 and ranges from about 10 to about 16 mer. In an alternative embodiment the peptide is a 16mer azido-peptide derived from the C3d region 1217–1232. The peptide may comprise 8-azido-adenosine attached to alpha or epsilon primary amine, 5-azido-tryptophan or 6-azido-tryptophan. The peptide may be bound to an antibody which is a full-length immunoglobulin molecule or a variable domain fragment of an antibody. The antibody is preferably specific for a cellular receptor, on a membrane structure such as a protein, glycoprotein, polysaccharide or carbohydrate, and on a normal cell or on tumor cells.

In the method of the invention the photo-chemical reaction may be mediated by a photo chemical compound selected from azido derivatized adenosine, ATP and tryptophan. The photo-chemical compound has an affinity for a hydrophobic structure in the variable domain of antibodies which binds to nucleotides or nucleosides.

The use of peptides derived from the ligand site of C3d as an immunostimulatory component incorporated into antibodies has an unexpected utility as a molecular adjuvant. C3d has been used as molecular adjuvant as part of a complete fusion protein with hen egg lysozyme (HEL) by D. Fearon, et al., (Dempsey, P. W., Allison, M. E. D., Akkaraju, S., Goodnow, C. C. and Fearon, D. T., Science, 271:348, 1996). These authors have shown that a HEL- C3d fusion protein is up to 10,000 fold more immunogenic than free HEL (see International Patent Publication, WO96/17625).

Similar increases in immunogenicity have been observed with chemical cross-linked idiotype vaccines using a peptide derived from the C3d fragment in our recent animal studies (see examples below). It is believed that attaching C3d peptides to idiotype and anti-idiotype vaccines enhances the immunogenicity of these vaccines and substitutes for the need of attaching carrier molecules such as KLH in combination with strong adjuvants such Freund adjuvant which is not permitted by the FDA for humans. In an alternative embodiment the peptide may be derived from a human or non-human C3d region homologous to the human C3d residues at position 1217–1232 and ranges from about 10 to about 16 mer.

Other applications of affinity cross-linking biologically active peptides to antibody vaccines include active peptides derived from cytokines. For example, a nonapeptide from the IL1-beta cytokine has been described (Antoni, et al., J. Immunol, 137:3201–04, 1986) which has immunostimulatory properties without inducing undesired side effects. Other examples of active peptides which can be inserted into antibodies in accordance with the invention include signal peptides, antigenic peptides, and peptides from the selfbinding locus of antibodies.

Two methods are used to affinity cross-link peptides to antibodies. In the first method azido-adenosine is oxidized with periodite to produce azido-adenosine-dialdehyde. The dialdehyde is reacted via a Schiff-base reaction to the primary amines of peptides (alpha and epsilon amino groups). The chemical bound is stabilized by a mild reducing reagents, such as borohydrate (see scheme I).

Scheme I

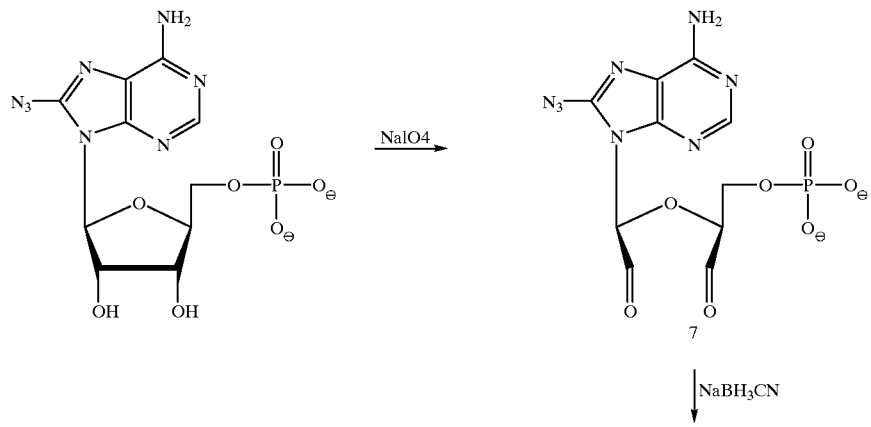

-continued

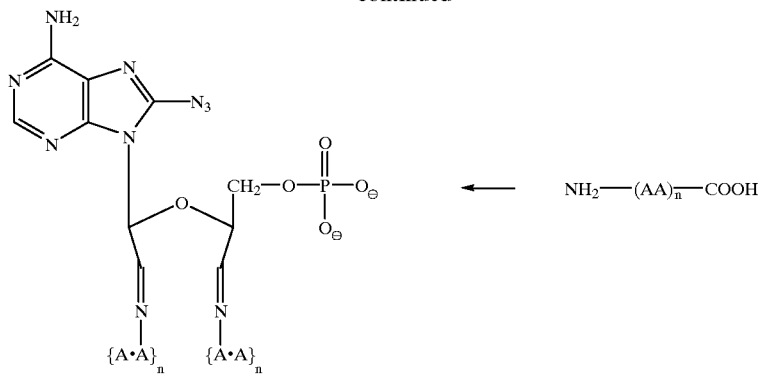

The azido-adenosine-peptide is photolyzed with UV light into the affinity site of antibodies. Since each antibody has two variable domain structures, two molecules of peptides can be photo-inserted into one molecule of antibody. 6-Azido-L-tryptophan is synthesized according to Miles and Phillips (Miles, E. W. & Phillips, R. S., *Biochemistry* 24: 4694–703, 1985). A variety of peptides are known having biological activities as hormones, ligands for cytokines or binding sites derived from natural ligands for cellular receptors. Also peptides have been recognized which represent the major antigenic determinants of proteins for stimulating B-cells to produce antibodies or for T-cells to generate helper of cytolytic T- cells. These peptides can be targeted to selected cellular targets via complexes consisting of affinity-cross-linked antibodies against specific cellular receptors on normal cells or to tumor cells. By targeting active peptides to specific targets biological or immunological processes can be induced without systemic side effects due to non-specific systemic deliveries.

For example, the present inventors have attached peptides, which represents the active binding region of complement to complement receptors on B-cells, to an antibody idiotype vaccine. This peptide-antibody complex increased the immunogenicity of the anti-idiotype vaccine, simulating the adjuvant effect of Freund's adjuvant or conjugation to a carrier protein, such as keyhole lympet hemocyanin (KLH).

The method of making and using the affinity-cross-linking C3d derived peptides has been demonstrated in two systems in animal experiments.

EXAMPLE 1

Enhancement of an anti-idiotype vaccine.

3H1 is a murine anti-idiotype antibody (Bhattacharya-Chatterjee, et al., *J. Immunol.*, 145:2758–65, 1990) which mimics the carcino-embryonic antigen (CEA). 3H1 induces in animals anti-CEA antibodies when used as KLH-conjugated vaccine in complete Freund's adjuvant. 3H1 has also been tested in a clinical phase I study where it induces antibodies which bind to CEA in approximately half of treated cancer patients. However no clinical response was observed in this study (Foon, et al., *J. Clin. Invst.*, 96:334–342, 1995) due, in part, to low immunogenicity.

3H1 mAb was affinity cross-linked with a 13 mer peptide derived from the C3d region 1217–1232. The amino acid sequence was derived from of the Cd3 peptide -KNRWEDPGKOLYNVEA-SEQ ID NO:1. BALB/c mice were immunized twice with 25 ug of C3d-3H1 in phosphate-saline solution intramuscular. 7 days after the last immunization mice were bled and sera were tested for binding to 8019 (Ab1 idiotype) and to the CEA expressing tumor line LS174T. As seen in FIG. 1 sera from C3d-3H1 immune mice bind to LS174T tumor cells as determined in FACS, while a control serum (normal mouse serum) showed only background fluorescence.

Sera from mice immunized with C3d-3H1 were used in FACS of LS174T cells in a sandwich assay developed with FITC conjugated goat anti-mouse IgG (FIG. 1). Control is a normal mouse serum. Cell number analyzed are plotted against relative fluorescence intensity on log10 scale.

EXAMPLE 2

Figure 2:
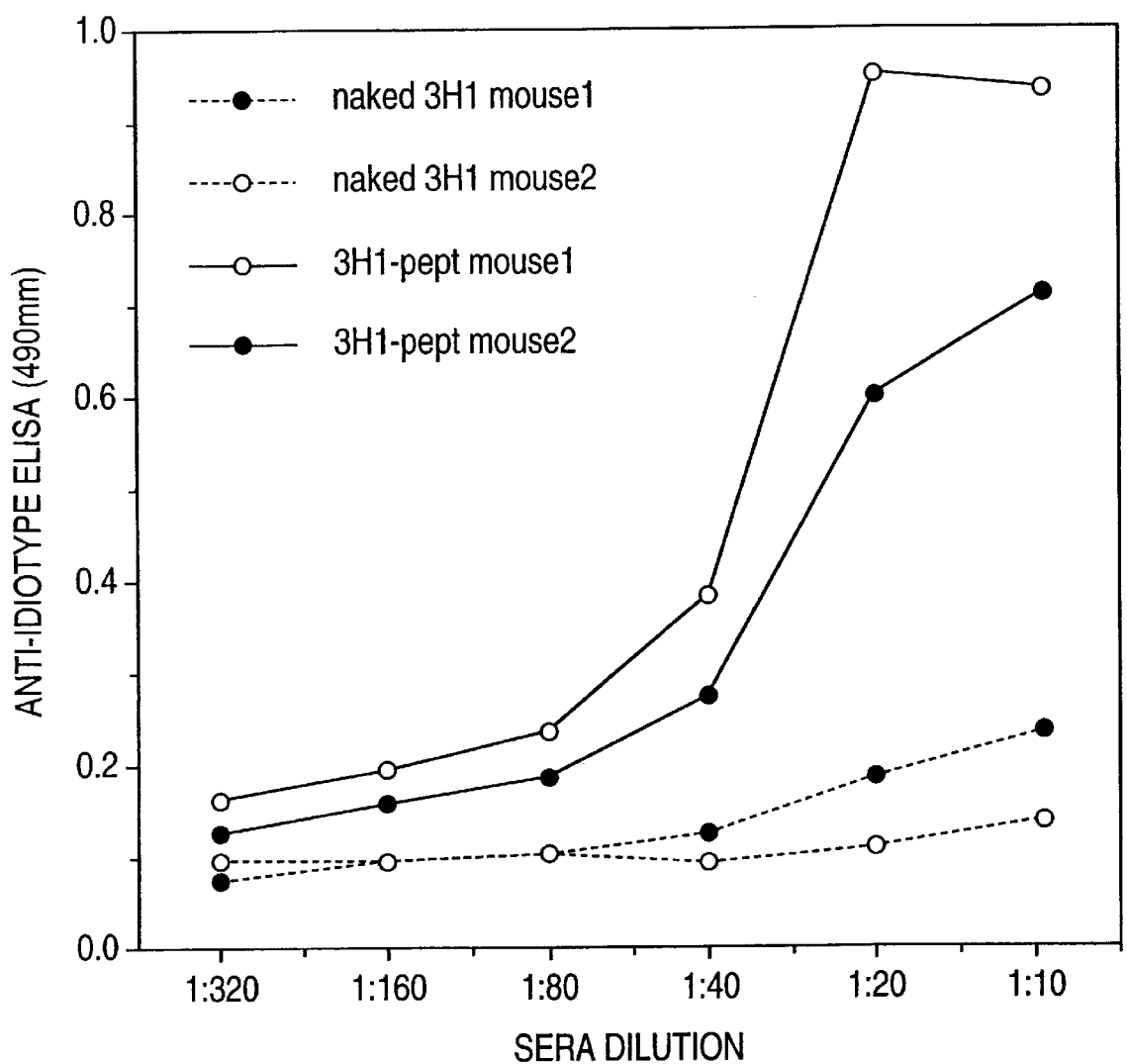
FIG. 2 shows two mice were immunized three times with 3H1 and two other mice with the 3H1-C3d peptide. Binding of sera dilutions of F(ab) of 3H1 as measured by ELISA is shown.

Furthermore, sera from mice immunized three times with either 3H1 (25 microgram in saline) or 3H1-C3d-peptide (affinity cross-linked, 25 microgram in saline) were also tested for Ab3 response. Mice were bled and sera were tested for binding to F(ab) of 3H1 in ELISA. FIG. 2 shows the binding of dilutions of mouse sera to 3H1 F(ab). While naked 3H1 does not induce Ab3 antibodies, 3H1-peptide does show that the affinity-cross-linked 3H1 enhanced immunogenicity. Other C3d peptides which may be used in the practice of the present invention include those reviewed in Lambris et al, "Phylogeny of the third component of complement, C3" in Erfi, A ed. New Aspects of Complement structure and function, Austin, R.D. Landes Co., 1994 p. 15–34, incorporated herein by reference in its entirety.

EXAMPLE 3

Human C3 is the most abundant complement in serum (1–2 mg/ml). It has been characterized as a glycoprotein comprised of a 115 kDa α chain linked to a 75 kDa β chain by a single disulfide bond and noncovalent forces (Scheme 2.1) below. The primary structure, deduced from the CDNA sequence consists of 1,633 amino acids, including a 22 amino acid signal peptide. Molecular modeling of C3, based on data derived from X-ray scattering studies depicts it as a two-domain shape, with a flat ellipsoid associated with a smaller flat domain. These two domains move closer together following proteolytic activation of C3 and removal of C3a. Carbohydrate analysis revealed that human C3 possesses 2 N-linked carbohydrate moieties, positioned at residues 63 of the β chain (Man5ClcNac2+Man6GlcNac2) and 917 of the α chain (Man8GlcNac2+Man9ClcNac2), which together account for 1.5% of the molecular weight of C3 (Scheme 2.1).

One of the distinguishing characteristics of C3 is its ability to bind covalently to acceptor molecules on cell surfaces via ester or amide linkages. This feature has been attributed to the thioester bond present within the C3d region of C3 which is sensitive to nucleophilic attack. The thioester bond is the product of an intramolecular transacylation between the thiol group of cysteine and the gamma-amide group of the glutamine within the C3 sequence Gly-Cys998-Gly-Glu-Gln991-Asn8. This thioester moiety is also found in C4 and α2-macroglobulin (α2-M), two plasma proteins homologous to C3. In native C3, the thioester group appears to be protected within a hydrophobic pocket and is exposed in the C3b fragment upon cleavage of C3 by C3 convertase. Thus, the transiently expressed thioester group can then participate in a transacylation reaction with nucleophilic groups present on cell surfaces, complex carbohydrates, or immune complexes. The deposition of C3b to surface structures is important for initiation of membrane attack complex (MAC), for phagocytosis of foreign particles, and for enhancement of effector cell-target cell contact. Cleavage of C3 between residues 726 and 727 (Arg-Ser) by either the classical (C4b,2a) or the alternative (C3b,Bb) pathway C3 convertases leads to the generation of C3b(185,000 kDa) and C3a (9,000 kDa). In contrast to native C3, C3b expresses multiple binding sites for other complement components, including C5, properdin (P), factors H, B, and I, C4 binding protein (C4bp), CR1 (C3b-receptor), and the membrane cofactor protein (MCP). Binding of these proteins to C3b leads either to amplification of the C3 convertase (by B and P in the presence of factor D) and initiation of the membrane attack complex (C5), or to the inactivation of C3b (by factor I). Whether amplification or inactivation occurs depends on the nature of the surface to which C3b is fixed.

The inactivation of C3b by factor I, an event by which complement activation is downregulated, proceeds in three steps and requires one of several cofactor molecules (MCP, CR1, CR2, H or C4bp). The cleavage of the a chain of C3b first between residues 1281–1282 (Arg-Ser) and then between residues 1298–1299 (Arg-Ser) of C3 liberates the C3f fragment (Mr2000) and yields iC3b. A third factor I cleavage site, with CR1 or factor H serving as cofactors, has been reported to exist at residues 932–933 (Arg-Glu) of the α chain of C3, generating the C3c and C3dg fragments.

The C3 fragments, both soluble and/or surface bound, generated during complement activation have the potential to bind specifically to several cell surface receptors, known as CR1, CR2, CR3, CR4, CR5, and C3a receptor. These C3-receptor interactions lead to various biological responses.

C3 is synthesized as a single chain prepro molecule with a and β chains linked by a tetra-arginine sequence which is removed by a furin-like enzyme during post-translational modification. Following translocation through the endoplasmic reticulum to the Golgi, N-linked high mannose type carboxyhydrate moieties are attached at the α and β chain (Scheme 2.1). The vast majority (more than 90%) of C3 biosynthesis occurs in the liver, but synthesis at numerous other sites may be involved in localized inflammatory processes. C3 expression is regulated by cytokines such as interferon (ICN), interleukin-1 (IL-1), and tumor necrosis factor (TNF). Regulation of C3 synthesis appears to be tissue-specific as in the cases of estrogen regulation in the uterus or vitamin D regulation in osteoblasts.

Studies of allelic variants of C3 have demonstrated the existence of 22 different variants, the most common of which are C3F and C3S. The 41-kb gene for human C3 has been localized to chromosome 19. Of the 41 exons (ranging in size from 52–213 bases) contained in the gene, 16 are in the β chain and 25 are in the α chain. Each of the major binding sites in the α chain of C3 appear to be encoded by single exons. The highly observed thioester domain is encoded by class 1-1 exons, the type most commonly reshuffled and duplicated. Coding regions of C4 and C5 also contain approximately 40 exons. The exons flanking the thioester site in C4 are similar to those of C3.

Rarely occurring, inherited C3 deficiencies are characterized by a heightened susceptibility to bacterial infections that lead to purulent lesions. In addition, several C3-deficient patients have shown impaired chemotactic activity, sluggish response o neutrophils to infectious agents, and development of immune complex disease, systemic lupus erythematosus, and membrane proliferative glomerulonephritis. Although the antibody response to routine immunizations is normal, an impaired switch from IgM to IgG was observed in two C3-deficient patients immunized with limited doses of the T=dependent antigen, bacteriophage φX174. A similar defective antibody response was observed in C3-deficient guinea pigs and in dogs. These findings and those made using pharmacologically C3-depleted animals suggest that C3 may play an important role in the generation of a normal immune response.

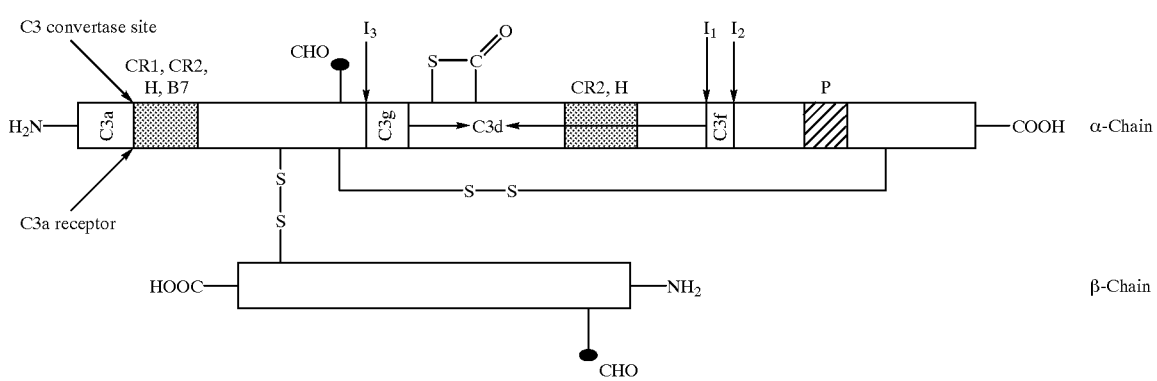

Scheme 2.1

-continued

Schematic representation of the C3 molecule. Human C3 consists of an α chain linked to a β chain by a disulfide bond. N-linked high-mannose carbohydrate moieties are present at residues 917 (a chain) and 63 (β chain) of C3. An internal thioester bond is located within the C3d region. Binding sites for receptors (CR1, CR2) and regulatory proteins (H, B, properdin) as well as conglutinin are shown. The factor I ($I_1$, $I_2$, $I_3$) and convertase cleavage sites are shown by arrows.

Scheme 2.2

```
            C3 CONVERTASE        K.I.?       I#3    I7          I#1                    I#2
            723                  917                            1280
            │   ↓                │   ↓       ↓      ↓           │  ↓       C3f         ↓
HUMAN   C3  GLARSNLDED ...II  // NATVAVRTLD  FERLGREGVQ KEDIPPA // SRSSKITHRI HWESASLLRS EETK
RABIT   C3  ******* ...   // *******   NQG* ES* // **PVKH V*D**** **
RAT     C3  *****DV*** ...**  // **********  **E*NQG*** R**VNA* // ****PTVF*L L***G**** ****
MOUSE   C3  *****E*E ...  // ***IH*  KQG*** *V*V*A* // ****AT*F*L LNGN* ****
G.PIG   C3  ***DM* ...  // *I*N  QQG*** R*E**A* // ****PSKF*L VAG** *A**
CHICKEN C3  E****EV*DA ...FL  // E*KIVE  *KTNN* EVKVRA* // R*ANAY ENNN*LVA A*
COBRA   C3  F****DFEDE ...LF  // KNI*TIIE**  *SVK*VG*T* ELTVIAN // E*EVPERYS* NDRN*VQA*T V***
TROUT   C3  .*S**EE*D* DDAYM  // K*ETN*LL..  .NPVKHG*E* TSH**SG // G*A*VTKWS* NNKNQFHT*T DKVN
HAGFISH C3  D*G**QG.** ..FM*  // EMS...*SWS  VQPRRHG*Q* VIVVDNE // ENGVFDXEFQ ITNDNAFVQK PFXV
LAMPREY C3  V*R*NDFM*. .LDLM  // IRS...ESRS  VEV...EERE TFFIKNE // KNN.FEKKMK IT*ETRFVQE PHXI
```

Amino acid sequence comparison of C3 convertase and factor I cleavage sites between C3 from different species and human. Numbering of the human C3 residues is adapted from DeBruiijn and Fey[2] after the signal peptide is subtracted. Asterisks indicate identical residues and periods indicate gaps introduced for maximal sequence alignment. The factor I($I_1$, $I_2$, $I_3$), kallikrein, and convertase cleavage sites are shown by arrows. I? indicates putative factor I cleavage sites.

Enhancement of an mouse Tumor Idiotype Vaccine (38C13).

38C13 is the idiotype expressed by the 38C13 B-lymphoma tumor cell line. The Levy group has developed this idiotype tumor vaccine model and has shown that pre-immunization with KLH-conjugated 38C13 Id can protect against challenge with 38C13 tumor cells in mice (Kaminski, M. S., Kitamura, K., Maloney, D. G. and Levy, R., *J. Immunol*, 138:1289, 1987). Levy and colleagues (Tao, M-H. and Levy, R., *Nature* 362:755–758, 1993) have also reported on the induction of tumor protection using a fusion protein (CSF-38C13), generated from a chimeric gene and expressed in mammalian cell culture fermentation. 38C13 Id proteins was affinity cross-linked with a 16 mer azido-peptide derived from the C3D region 1217–1232.

Figure 3:
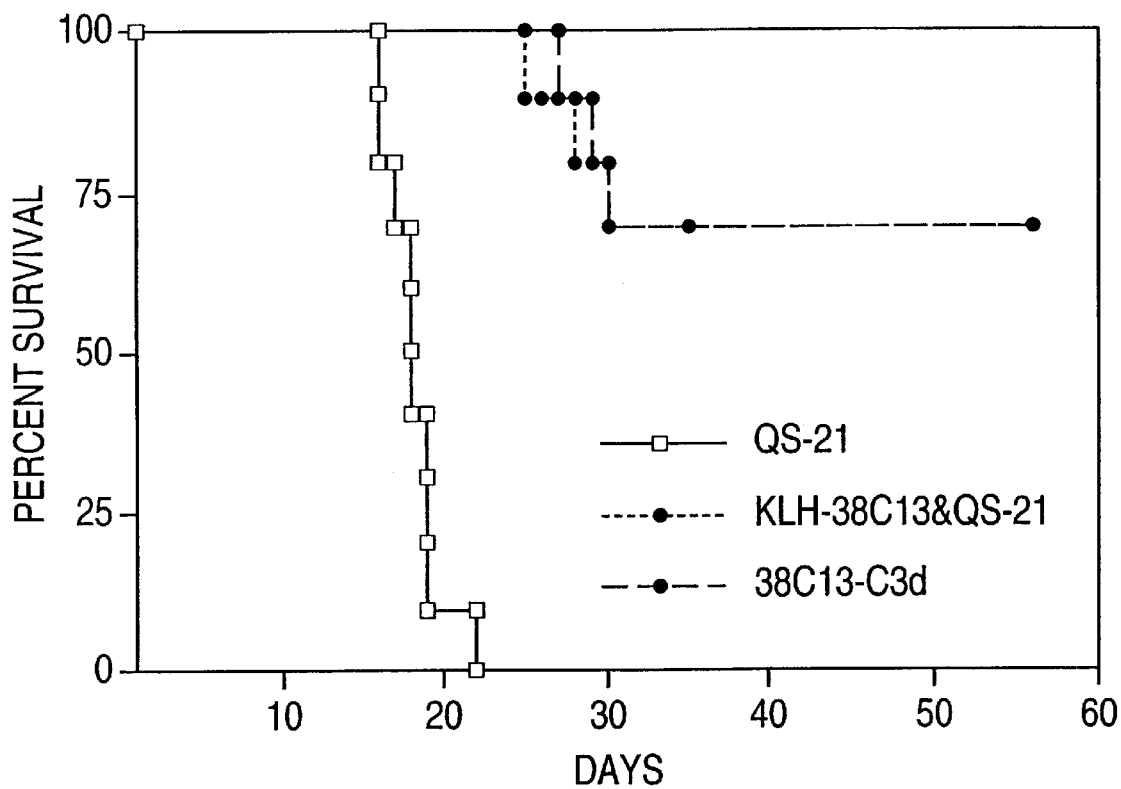
FIG. 3 shows a tumor survival plot (Kaplan-Meier Plot) of mice pre-immunized with a) QS-1 (adjuvant), b) KLH-38C13 conjugate and QS-1 and 38C13-C3d peptide conjugate. Mice were immunized three times intraperional with 50 microgram conjugates or QS-1 solution. Mice were challenged with 38C13 tumor cells and survival was monitored. Ten mice were in each group.

10 mice were immunized with 50 ug of C3d-38C13 conjugate in phosphate-saline solution intraperitoneally three times. After the third vaccination mice were challenge with 38C13 tumor cells. Control groups included mice vaccinated with 38C13-KLH in QS-21 (adjuvant), considered the "gold standard" in this tumor model, and mice injected with QS-21 alone. As seen in FIG. 3, 7 out 10 mice vaccinated with the C3d-38C13 conjugate survived by day 35 after tumor challenge, as did mice vaccinated with the KLH-38C13 in QS-21. All control mice injected only with QS-21 had died by day 22.

C3H mice were immunized three times with either 38C13-KLH in QS-21 or with 38C13-C3d peptide without QS-21 (50 ug i.p.) Control mice were only injected with QS-21. Immunized and control mice were than challenged with 38C13 tumor cells and survival was monitored (FIG. 3).

Results illustrated in Examples 1–3 show that affinity-cross-linking of an immuno-stimulatory peptide to tumor anti-idiotype and idiotype vaccine antibodies can significantly enhance the immune response to the tumor and protect against tumor challenge. The vaccination protocol with the C3d-cross-linked vaccine did not include any adjuvant, such as Freund's adjuvant, or KLH conjugation, both of which are not permissible by the FDA for human use.

EXAMPLE 4

Enhanced antigen presentation by an affinity cross-linked T-cell epitope peptide.

The peptide derived from the sequence 323–339 of ovalbumin (OVA) is one of the major T-cell epitopes in mice. A mouse T-cell hybridoma BWZ.36 clone responds with activation of beta-gal producing color with x-gal substrate when challenged with the T-cell peptide in vitro in the presence of presenting B-cells. The dose of OVA peptide for maximum response is in the 5–10 microgram/ml. In order to improve presentation of the peptide to T-cells the ability of anti-Ig antibodies to target the peptide to the presenting B-cells was enhanced. This was achieved by affinity-cross-linking the peptide to an anti-Fab antibody. Peptide-conjugated antibody induced maximum response at a peptide concentration of 0.01 ug/ml. Thus T-cell epitope peptide presented by anti-Ig to B-cells reduces the peptide dose more than 1000 fold. It is believed that the peptide-anti-Fab binds to the B-cell receptor on B-cells and is internalized induced by cross-linking the Ig receptor followed by uptake of the receptor antibody complex.

The following cultures were assayed: 1. Peptide, presenting B-cells were incubated with T-cell peptide at indicated concentration; peptide and Ig (50 ug), peptide together with 50 microgram of normal mouse IgG; Fab-peptide, anti-Fab IgM affinity-cross-linked with T-cell peptide; Fab-peptide and Ig50 ug, anti-Fab IgM affinity-cross-linked with T-cell peptide together with 50 microgram of normal mouse IgG; peptide and Ig10 ug, peptide together with 10 microgram of normal mouse IgG; Fab-peptide and Igloug, anti-Fab IgM affinity-cross-linked with T-cell peptide together with 10 microgram of normal mouse IgG.

EXAMPLE 5

Azido-tryptophan is shown to compete with the nucleoside affinity-photobiotinylation. In order to demonstrate that azido-tryptophan containing peptides can be cross-linked to the nucleoside affinity site competition photobiotinylation experiments were performed. As seen in FIG. 5, 6-azido-tryptophan competes with 8-azido-adenosone-biotin effectively.

Some of the procedures used in the above examples are known; for more detail see, a method of using azido-adenosine and Azido-ATP has been described by Pavlinkova, et al., (*J. Immun. Methods,* 201:77–88, 1997). The active binding peptide of C3d (complement fragment) has been described by Lambris, et al., (*PNAS,* 82:4235–39, 1985) and is incorporated herein by reference in its entirety. The synthesis of 5-azido-tryptophan has been described by Miles & Phillips (Miles, E. W. & Phillips, R. S., Biochemistry 24:4694–703, 1985).

Figure 4:
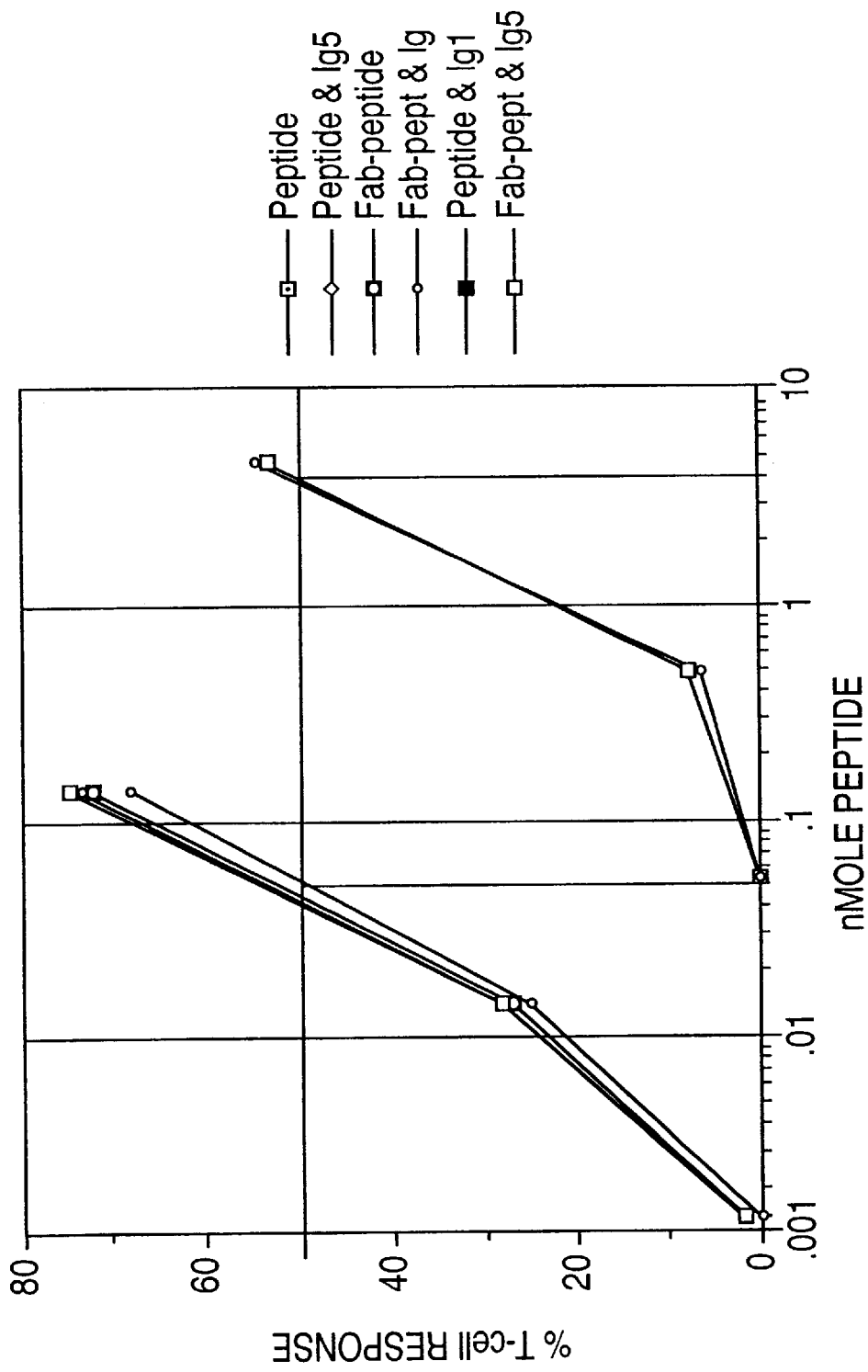
FIG. 4 shows that hybridoma BWZ.36 cells were co-cultured with purified mouse B-cells for 24 or 48 hrs. Response of T-cells is expressed as percentage of maximum response using x-gal assay. The percent (%) T-cell response is plotted against amount of peptide used. This result shows that affinity cross-linking of T-cell antigen peptide to antibodies which target presenting cells can significantly reduce the amount of effective peptide antigen and thereby reduce the need for immuno-stimulatory adjuvants.

As seen in FIG. 4, the amount of T-cell peptide needed in the in vitro T-cell response is more than two logs lower, compared to added free peptide, if the peptide is conjugated to the anti-Fab antibody which delivers the peptide to the presenting B-cells. Hybridoma BWZ.36 cells were co-cultured with purified mouse B-cells for 24 or 48 hrs.

Prior to this culture B-cells had been exposed to goat ant-Fab IgM, mixtures of peptide and ant-Fab IgM and ant-Fab IgM-peptide complex. Response of T-cells is expressed as percentage of maximum response using x-gal assay. % T-cell response is plotted against amount of peptide used.

This result shows that affinity cross-linking of T-cell antigen peptide to antibodies which target presenting cells can significantly reduce the amount of effective peptide antigen and thereby, advantageously and unexpectedly reduces the need for immuno-stimulatory adjuvants. While non-site-specific peptide conjugation to targeting antibodies may also induce similar immuno-enhancing effects, the affinity-site specific cross-linking preserves the critical antigen binding site of targeting and delivering antibodies. This property represents an advantage over conventional cross-linking methods by reducing the effective dose of peptide-conjugated antibody preparation.

The results illustrated in Examples 1 to 5 above, demonstrate that affinity-cross-linking of immunologically active peptides to antibodies can result in enhancement of immunogenicity of idiotype antibody vaccines and improvement of peptide presentation to T-cells. These advantages are useful in the design of novel and more efficient anti-tumor or anti-microbe vaccines for treating human diseases. The key to such improved prophylactic and therapeutic vaccines is the unique method of affinity-cross-linking peptides into a site on antibodies which does not interfere with antigen binding and preserves the structural and functional integrity of the antibody molecule.

Thus invention also provides a composition and a pharmaceutical composition comprising a photochemically activated peptide having an N or C terminal azido compound, wherein said N or C terminal azido compound is crosslinked to an antibody and said azido compound has an affinity for a hydrophobic structure in the variable domain of said antibody which binds to nucleotides or nucleosides, binding said peptide into a native binding pocket of the immunoglobulin (Ig) structure of an antibody, and wherein the site of cross-linking is located away from the antigen binding site in the Fv domain avoiding the compromise of antigen recognition.

Any antibody may be used in the peptide/antibody complex of the invention. Preferred antibodies are anti-idiotype antibodies. For example, anti-idiotype antibody 3H1 may be used (see "Anti-idiotype Antibody Vaccine (3H1) that Mimics the Carcinoembryonic Antigen (CEA) as an Adjuvant Treatment", Foon, et al., *Cancer Weekly,* Jun. 24, 1996). Other anti-idiotype antibodies which may be used in the present invention include, for example, anti-idiotype antibody to chlamydia glycolipid exoantigen (U.S. Pat. No. 5,656,271; anti-idiotype antibody 1A7 for the treatment of melanoma and small cell carcinoma (U.S. Pat. No. 5,612,030); anti-idiotype antibody MK2-23 anti-melanoma antibody (U.S. Pat. No. 5,493,009); anti-idiotypic gonococcal antibody (U.S. Pat. No. 5,476,784) Pseudomonas aeruginosa anti-idiotype antibody (U.S. Pat. No. 5,233,024); antibody against surface Ig of Human B cell tumor (U.S. Pat. No. 4,513,088); and monoclonal antibody BR96 (U.S. Pat. No. 5,491,088). In a preferred embodiment the molar concentration of the cross-linking peptide is about 150 micro Moles. Any restrictions on peptide length are those practical limitations associated with peptide synthesis and not restrictions associated with practice of the method of the invention.

In an alternative embodiment, self-binding peptides such as those disclosed in (Kang, C. Y. Brunck, T. K., Kiever-Emmons, T., Blalick, J. E. and Kohler, H., "Inhibition of self-binding proteins (auto-antibodies) by a VH-derived peptide, Science, 240: 1034–1036, 1988, incorporated herein by reference in its entirety) used in the method of the present invention.

Additionally signal peptide such as those disclosed in Roias, et al., "Genetic Engineering of proteins with cell membrane permeability", Nature Biotechnology, 16: 370–375 (1988) and Calbiochem Signal Transduction Catalogue 1997/98, incorporated herein by reference in their entireties, may be used in the method of the invention.

Moreover, antigenic peptides such as that disclosed in Pincus et al, "Peptides that mimic the group B streptococcal type II capsular polysaccharide antigen", J. Immunol., Vol 160: 293–298 (1998) [incorporated herein by reference in its entirety] may be substituted for the C3d peptide in example 1, and may be used in the practice of the present invention.

The compositions of the invention are useful in pharmaceutical compositions for systemic administration to humans and animals in unit dosage forms, sterile solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. The compositions are useful in pharmaceutical compositions (wt %) of the active ingredient with a carrier or vehicle in the composition in about 1 to 20% and preferably about 5 to 15%.

The above parenteral solutions or suspensions may be administered transdermally and, if desired a more concentrated slow release form may be administered. The cross-linked peptides of the invention may be administered intravenously, intramuscularly, intraperitoneally or topically. Accordingly, incorporation of the active compounds in a slow release matrix may be implemented for administering transdermally. The pharmaceutical carriers acceptable for the purpose of this invention are the art known carriers that do not adversely affect the drug, the host, or the material comprising the drug delivery device. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 10 to 500 mg, preferably 2–15 mg, when administered by suspension at least once daily. Administration may be repeated at suitable intervals.

The purpose of the above description and examples is to illustrate some embodiments of the present invention with-

What is claimed is:

1. A method of affinity cross-linking a peptide to an antibody so that the peptide becomes attached to the antibody at a location where the peptide does not compromise the antigen recognition of the antibody, the method comprising the steps of (a) providing an antibody, the antibody having a variable domain, the variable domain including a hydrophobic structure, the hydrophobic structure defining a binding pocket having a tryptophan-binding site, and wherein the hydrophobic structure is located away from the antigen binding site that is in the Fv domain of the antibody, (b) providing a peptide that has an azido tryptophan residue, the azido tryptophan residue having an affinity for the hydmphobic-:structure of the variable domain of the antibody, (c) photo-chemically activating the azido tryptophan residue of the peptide, and (d) allowing the peptide and the antibody to interact whereby the photo-chemically activated azido tryptophan residue binds to the hydrophobic structure of the variable domain and reacts with the tryptophan-binding site whereby the peptide becomes cross-linked to the antibody, whereby, because the location of the hydrophobic structure is away from the antigen binding site that is in the Fv domain of the antibody, the cross-linked peptide does not compromise the antigen recognition of the antibody.

2. The method of claim 1 wherein the azido tryptophan residue is a 5-azido tryptophan residue or a 6-azido-tryptophan residue.

3. The method of claim 1 wherein the peptide that has an azido tryptophan residue is formed by providing a peptide that initially does not have an azido tryptophan residue and then adding an azido tryptophan residue to the C-terminal or N-terminal of the peptide.

4. The method of claim 1, wherein each antibody has two variable domain structures and wherein steps (c) and (d) are carried out so that two molecules of the peptide are attached to each molecule of the antibody.

5. The method of claim 1, wherein the peptide is derived from a human or non-human C3d region homologous to the human C3d residues at position 1217–1232 and ranges from about 10 to about 16 mer.

6. The method of claim 1, wherein said peptide is a 16 mer azido-peptide derived from the a human or non-human C3d region homologous to the human C3d residues at position 1217–1232.

7. The method of claim 1, wherein said peptide has a biological activity selected from the group consisting of immuno-stimulatory, membrane transport, homophilic and antigenic activities.

8. The method of claim 1, wherein said peptide is derived from the binding site region of cytokines or complement fragments.

9. The method of claim 1, wherein said peptide comprises immunogenic epitopes for T-cells or B-cells.

10. The method of claim 1, wherein said antibody is specific for a cellular receptor, on a membrane structure on a normal cell or on tumor cells.

11. The method of claim 1, wherein said antibody is a full-length immunoglobulin molecule or a variable domain fragment of an antibody.

12. The method of claim 1, wherein the peptide is selected from the group consisting of hormones, ligands for cytokines and binding sites derived from natural ligands for cellular receptors.

13. A composition consisting essentially of a pcptide that has a 5-azido tryptophan or 6-azido tryptophan residue cross-linked to an antibody, wherein the peptide is attached to the antibody at a location where the peptide does not compromise the antigen recognition of the antibody, the composition being made by a proccss comprising the steps of (a) providing an antibody, the antibody having a variable domain, the variable domain including a hydrophobic structure, the hydrophobic structure defining a binding pocket having a tryptophan-binding site, and wherein the hydrophobic structure is located away from the antigen binding site that is in the Fv domain of the antibody, (b) providing a peptide that has an azido tryptophan residue, wherein said azido tryptophan residue is 5-azido tryptophan or 6-azido tryptophan, the azido tryptophan residue having an affinity for the hydrophobic structure of the variable domain of the antibody, (c) photo-chemically activating the azido tryptophan residue of the peptide, and (d) allowing the peptide and the antibody to interact whereby the photo-chemically activated azido tryptophan residue binds to the hydrophobic structure of the variable domain and reacts with the tryptophan-binding site whereby the peptide becomes cross-linked to the antibody, whereby, because the location of the hydrophobic structure is away from the antigen binding site that is in the Fv domain of the antibody, the cross-linked peptide does not compromise the antigen recognition of the antibody.

14. The composition of claim 13 wherein the peptide that has an azido trypophan residue is formed by providing a peptide that initially does not have an azido trypophan residue and then adding an azido trypophan residue to the C-terminal or N-terminal of the peptide.

15. The composition of claim 13 wherein said antibody is specified for a cellular receptor on a normal cell or on tumor cells.

16. The composition of claim 13 wherein said antibody is a full-length immunoglobin molecule or a variable domain fragment of an antibody.

17. A method of affinity cross-linking a peptide to a variable domain fragment of an antibody so that the peptide becomes attached to the variable domain fragment at a location where the peptide does not compromise the antigen recognition of the variable domain fragment, the method comprising the steps of (a) providing a variable domain fragment, the variable domain fragment including a hydrophobic structure, the hydrophobic structure defining a binding pocket having a tryptophan-binding site, and wherein the hydrophobic structure is located away from the antigen binding site that is in the Fv domain of the variable domain fragment, (b) providing a peptide that has an azido tryptophan residue, the azido tryptophan residue having an affinity for the hydrophobic structure of the variable domain fragment, (c) photo-chemically activating the azido tryptophan residue of the peptide, and (d) allowing the peptide and the antibody to interact whereby the photo-chemically activated azido tryptophan residue binds to the hydrophobic structure and reacts with the trytophan-binding site whereby the peptide becomes cross-linked to the variable domain fragment, (e) whereby, because the location of the hydrophobic structure is away from the antigen binding site that is in the Fv domain of the antibody, the cross-linked peptide does not compromise the antigen recognition of the variable domain fragment.

* * * * *